(12) United States Patent
LaPointe et al.

(10) Patent No.: US 7,494,674 B2
(45) Date of Patent: Feb. 24, 2009

(54) NUTRACEUTICAL WITH TART CHERRIES AND METHOD OF TREATMENT THEREWITH

(76) Inventors: Andrew T. LaPointe, 6175 Heldeldorf Dr., Bellaire, MI (US) 49615; Jennifer A. LaPointe, 6175 Heldeldorf Dr., Bellaire, MI (US) 49615

( * ) Notice: Subject to any disclaimer, the term of this patent is extended or adjusted under 35 U.S.C. 154(b) by 0 days.

(21) Appl. No.: 11/534,490

(22) Filed: Sep. 22, 2006

(65) Prior Publication Data

US 2008/0075797 A1 Mar. 27, 2008

(51) Int. Cl.
*A61K 36/736* (2006.01)
*A61K 31/737* (2006.01)
*A61K 31/7048* (2006.01)
*A61K 31/7008* (2006.01)
*A61K 31/353* (2006.01)

(52) U.S. Cl. .......................... 424/735; 514/27; 514/54; 514/62; 514/456

(58) Field of Classification Search .................. None
See application file for complete search history.

(56) References Cited

U.S. PATENT DOCUMENTS

| 5,670,200 | A | | 9/1997 | Pleva |
| 5,804,594 | A | * | 9/1998 | Murad ......................... 514/474 |
| 6,150,408 | A | | 11/2000 | Nair et al. |
| 6,566,389 | B1 | | 5/2003 | Zisapel et al. |
| 6,579,544 | B1 | * | 6/2003 | Rosenberg et al. .......... 424/736 |
| 6,656,925 | B2 | * | 12/2003 | Petrus .......................... 514/62 |
| 7,214,666 | B1 | * | 5/2007 | Madere ......................... 514/62 |
| 7,217,435 | B2 | * | 5/2007 | Smith .......................... 426/615 |

FOREIGN PATENT DOCUMENTS

| CN | 1408401 A * | 4/2003 |
| WO | WO 2004/004686 | 1/2004 |
| WO | WO 2006/015119 | 2/2006 |

OTHER PUBLICATIONS

Kelley, Darshan S., "Consumption of Bing Sweet Cherries Lowers Circulating Concentrations of Inflammation Markers in Healthy Men and Women," Journal of Nutrition, Apr. 2006, vol. 136, pp. 981-986.

* cited by examiner

*Primary Examiner*—Christopher R. Tate
(74) *Attorney, Agent, or Firm*—Vedder Price PC

(57) ABSTRACT

The present disclosure provides a nutraceutical for the use of a vacuolar flavonoid pigment from a natural source such as tart cherries as an additional compound as part of a mixture including at least an amino sugar, such as glucosamine, and a sulfated glycosaminoglycan, such as chondroitin sulfate. What is also contemplated is the use of the vacuolar flavonoid pigment in conjunction with other known joint regeneration nutraceuticals, including a mixture of glucosamine, chondroitin sulfate, and MSM, and a method of treatment of osteoarthritis.

3 Claims, No Drawings

NUTRACEUTICAL WITH TART CHERRIES AND METHOD OF TREATMENT THEREWITH

FIELD OF THE DISCLOSURE

The present disclosure relates generally to a nutraceutical for the protection of joints and muscles, and in particular, to a nutraceutical with two cartilage supplements and tart cherries, and a method of treatment therewith.

BACKGROUND

Good health is a leading concern of individuals. Advances in medicine and pharmaceutical science have increased human life expectancy and general wellbeing. New products having a beneficial effect on human health have proven usefulness and are in high demand. Hippocrates is quoted as saying, "let your food be your medicine and let your medicine be your food." In 1989, the term "nutraceutical" was coined from a combination of the terms "nutritional" and "pharmaceutical" and refers to nutritional foods having a beneficial effect on human health. What is known is that many natural foods have beneficial effects on human health and that scientific research is progressively unlocking the secrets of the plant kingdom and providing these advantages to mankind.

Many plant- or fruit-derived compounds, by their ability to serve as cellular antioxidants, anti-inflammatory agents by inhibiting prostaglandin synthesis, or inhibitors of enzymes involved in cell proliferation, impart important, positive nutriceutical and phytoceutical traits to mixtures and foods to which they are added. These abilities are important for a wide range of health benefits, including but not limited to amelioration of the spread of chronic diseases, reduction in arthritis, regeneration of ligaments and joints, aid with cardiovascular health, and much more. Chinese medicine is one example of a centuries-old nutriceutical therapy with recognized effects and proven usefulness. Recent research into new compounds allows researchers to isolate compounds, recognize their unique natures, and create novel nutraceuticals.

Research conducted at Michigan State University discovered a high level of anthocyanin in fruit and berries, especially in cherries and raspberries. (Seeram et al., Cyclooxygenas (2001)). The anthocyanins, perceived as the red pigment in cherries, have been shown to reduce pain and inflammation. (Behav. Brain s. (2004). 153(1): 181-188). These pigments have also been shown to be potent antioxidants with high levels of melatonin. (Burkhardt et al. (2002) Detection, J. Agric. Food Chem. 49(10): 4898-4902). The research on anthocyanin is ongoing and indicates that this compound may increase insulin production in the human body. To list only one usefulness, Nobel Prize laureate Julius Axelrod linked melatonin to circadian rhythms in humans. Tart cherries have been found to contain high levels of anthocyanin and melatonin. Tart cherries are also rich in phenolic compounds, catechins, chlorogenic acid, and flavonal glycoside. (Wang et al. (1999). Antioxidant, J. Nat. Prod. 62:294-6). U.S. Pat. No. 6,566,389 teaches a method of therapeutic use of melatonin to treat or prevent symptoms of tardive dyskensia. U.S. Pat. No. 6,150,408 teaches a new mixture of isomers of an antioxidant compound isolated from tart cherries where a hydroxyl and a hydrogen are placed at precise locations. International Patent Publication No. WO 2006/015119 teaches the use of tart cherry as an antioxidant in a emu oil composition for improved skin care products.

Known products for joint and muscle regeneration include combinations of glucosamine, chondroitin sulfate, and methylsulfonylmethane (MSM), three compounds naturally occurring in the human body's joints. Recent studies have shown that combinations of glucosamine and chondroitin sulfate are effective in osteoarthritis patients with moderate to severe knee pain. Glucosamine promotes the formation and repair of cartilage, and chondroitin sulfate promotes water retention and elasticity in joint cartilage. MSM is used to treat tendon soreness and inflammation.

Earlier studies suggested that MSM, used along with glucosamine sulfate at daily dose of 1,500 mg, would relieve symptoms of knee osteoarthritis. (Usha et al. (2004), Clin. Drug Invest. 24(6):353-63). However, recent studies have questioned the long-term safety and usefulness of MSM as an anti-inflammatory. (Kim et al. (2006). Osteoarthritis 14(3); 286-94). The manufacture of MSM is industrial and is purified from dimethylsulfoxide and hydrogen peroxide. The health effects of MSM, a high-temperature industrial solvent, when used as a joint regenerator are poorly understood at best. (Morton et al. (1986). Proc. Soc. Exp. Biol. Med. 183:227-30).

What is needed is a novel nutraceutical for the protection of joint and muscles that provides a natural replacement compound able to work in conjunction with known joint regeneration compounds, or a new replacement compound able to correct the defects of known joint regenerators associated with the industrial compound MSM.

SUMMARY

The present disclosure describes a nutraceutical that uses a vacuolar flavonoid pigment taken from a natural source, such as tart cherries, as compound added to a mixture including at least an amino sugar, such as glucosamine, and a sulfated glycosaminoglycan, such as chondroitin sulfate. What is also contemplated is the use of the vacuolar flavonoid pigment in conjunction with other known joint regeneration nutraceuticals, including a mixture of glucosamine, chondroitin sulfate, and MSM, and a method of treatment of osteoarthritis therewith.

DETAILED DESCRIPTION

Cherries selected for human consumption are derived primarily from two species: the wild cherry (*prunus avium*), which has given rise to the sweet cherry family to which most cherries belong, and the sour cherry, also known as tart cherry (*prunus cerasus*), which is used mainly in cooking and sweetened jams. Popular varieties of sweet cherries include the Bing cherry and the Black cherry. Varieties of tart cherries include the Montmorency, the Morello, and the Balatin cherry. Tart cherries contain anthocyanins and bioflavonoids, which inhibit the enzymes Cyclooxygenase-1 and -2 and prevent inflammation in the body. These compounds have activity similar to aspirin, naproxen, and ibuprofen. Daily consumption of cherries have the potential to reduce the pain associated with inflammation, arthritis, and gout.

Known supplements for joint regeneration include the use of glucosamine, chondroitin sulfate, and MSM. It is recognized that dietary cartilage supplements are effective in reducing the symptoms of joint pain. (Drovani, Clinical Therapeutics, (1980)). An amino acid complex combining glutamine with glucosamine sulfate is the constituent used by the human body to make cartilage and connective tissues, which cushions and lubricates the joints in the body. The Mayo Clinic confirms that glucosamine provides benefits in the synovial fluid by strengthening cartilage and aiding glycosaminoglycan synthesis. Glucosamine, glucosamine hydrochloride and glucosamine sulfate, glucosamine salts, glucosamine derivatives, and glucosamine hydrochloride are used as joint regeneration compounds under different circumstances. The World Health Organization has officially classified glucosamine sulfate as a slow-acting drug for the treatment of osteoarthritis. Typically, glucosamine sulfate is taken in the form of a pill or a powder. The daily recommended dose for the treatment of osteoarthritis as determined by studies should be taken orally in 1,500 mg tablets or capsules. This dose has been taken as a preferred embodiment. Dosing of 20 mg per kilogram of body weight has also been recommended. Glucosamine is classified by the U.S. Food and Drug Administration as a dietary supplement. The European Drug Agency has approved glucosamine as a drug. Glucosamine, also known as $C_6H_{14}NO_5$, is an amino sugar that is an important precursor in the biochemical synthesis of glycosylated proteins and lipids.

Chondroitin sulfate is a sulfated glycosaminoglycan composed of a chain of alternating sugars. Chondroitin sulfate chains are linked to hydroxyl groups on serine residues of certain proteins. Each monosaccharide may be left unsulfated, sulfated once, or twice sulfated. Most commonly, the hydroxyls of the 4 and 6 positions of the N-acetyl-galactosamine are sulfated. Sulfation is mediated by specific sulfotransferases. Chondroitin and chondroitin sulfate are other compound widely sold as agents for the treatment of joint pain. Chondroitin sulfate is also taken in pill or powdered form. The recommended daily dose when taken orally is 800 to 1200 mg tablets or capsules. In a preferred embodiment, a dosage of 1,200 mg is contemplated. These values are for a monotherapy for the treatment of osteoarthritis. Higher doses may reach 2,000 mg per day. Chondroitin sulfate is classified by the U.S. Food and Drug Administration as a dietary supplement. Chondroitin sulfate, when used in conjunction with glucosamine, improves symptoms, arrests, and reverses the degenerative process of osteoarthritis. What is contemplated as a chondroitin sulfate and the associated nonsulfated version includes all known types of chondroitin, including but not limited to chondroitin-4-sulfate, chondroitin-6-sulfate, dermatan sulfate, chondroitin-2,6-sulfate, chondroitin-4,6-sulfate, or even generically sodium chondroitin.

One other known joint regenerator is methylsulfonylmethane, also known as MSM or dimethylsulfone. MSM is an organic sulfur compound belonging to the class of sulfones. MSM is sold as a dietary supplement for preventing osteoarthritis, among other things. MSM is also used as a stable and polarized solvent in high-temperature industries for both organic and inorganic substances. Some commercial embodiments of joint and muscle supplements include Knox®, NutraJoint® Plus Glucosamine 1650 mg, NatureMade® Glucosamine 500 mg, NOW® Glucosamine Sulfate 750 mg (Glucosamine only supplement), Spring Valley® MSM 1000 mg, Naturally Inspired™ MSM 750 mg from Vitamin World® (MSM only supplement), Cosamin DS® Double Strength Joint Health 500 mg/400 mg, NOW® Extra Strength Joint Support Factors 750 mg/600 mg, Rexall® Osteo Bi-Flex Complex 750 mg/600 mg (Glucosamine and Chondroitin supplements), Maximum Strength Flex-a-min® 500 mg/400 mg/166.7 mg, Nature Made Triple Flex Triple Strength Supplement 750 mg/600 mg/125 mg, and Puritan's Pride Dietary Supplement 500 mg/400 mg/125 mg (Glucosamine, Chondroitin, and MSM). Each of these concentrations are given per capsule and not per daily allowance.

Anthocyanin is a water soluble vacuolar flavonoid pigment that appears to be either red or blue based on surrounding pH. Anthocyanin is found in a variety of plants and fruits. Many uses have been observed for anthocyanins, including ultraviolet ray protectors, ultraviolet absorbers, and tissue photoinhibition, and anthocyanins are responsible for the red autumn coloration of leaves once green chlorophyll breaks down in a leaf. Some fruits, such as the cherry which exhibits a deep or vibrant red color, contain very high quantities of anthocyanins. Anthocyanins are also used to prevent tissue inflammation and protect arterial walls from damage that leads to plaque build-up and heart disease. Testimonial evidence corroborates the pain relief associated with daily absorption of anthocyanin. Anthocyanins include anthocyanidine aglycons and the anthocyanin glycosides. As a food colorant, anthocyanins are given the code E-163. Concentration of anthocyanin varies with the age of the plant or fruit to be harvested and is highly dynamic. Anthocyanins 1 and 2, blockers of Cyclooxygenase-1 and -2, respectively, are present in cherries in concentrations of 26.5 mg to 24 mg per 100 grams of cherry. (Seeram et al. (2001) Phytomedicine 8(5):362-9)). In one preferred embodiment, a daily dosage of 425 mg of tart cherry is contemplated based on testimonial experience of pain relief in joints. While one dose has been found to be useful and leads to adequate joint and muscle repair properties, what is contemplated is any dose ultimately found to contain sufficient levels of anthocyanin to relieve pain in an individual.

High levels of melatonin have also been observed in tart cherry. Melatonin, or 5-methoxy-N-acetyltryptamine, is a hormone found in living creatures and algae. Levels up to 0.0135 mg of melatonin per gram of cherry has been observed in the *prunus cerasus* family. Burkhardt (2001). Melatonin also works as an antioxidant and has also other known health-related effects.

What is contemplated is a nutraceutical for human consumption, the nutraceutical being formed from a mixture of an amino sugar, a sulfated glycosaminoglycan, and a vacuolar flavonoid pigment. In a preferred embodiment, the amino sugar is glucosamine, the sulfated glycosaminoglycan is chondroitin sulfate, and the vacuolar flavonoid pigment is anthocyanin obtained from tart cherry. While one possible contemplated mixture is described, what is contemplated is the use of any amino sugar and sulfated glycosaminoglycan in conjunction with a vacuolar flavonoid pigment. As a nonlimiting example, any fruit, flower, or plant where sufficient levels of anthocyanin are found can be used, such as rose petals, red wine, aubergine, red cabbage, and usambara violet. What is also contemplated is the use of sweet cherries of the prunus avium species or the use of any other cherry from the prunus cerasus species. In yet another preferred embodiment, the tart cherries are Montmorency cherries.

In one preferred embodiment, a capsule containing 1,500 mg of glucosamine, 1,200 mg of chondroitin sulfate, and 425 mg of tart cherry is contemplated for a weigh distribution in a capsule only containing these three components of 48% by weight of glucosamine, 38% by weight of chondroitin sulfate, and 14% by weight of tart cherries, respectively. While one possible formulation of these different ingredients is given, what is contemplated and what will be understood as the disclosed embodiment by one of ordinary skill in the art is any nutraceutical combination that remains within the recommended doses but results in an effective joint pain reduction therapy. An approximate value of ±5% is given as a possible acceptable variability for each component of the mixture, but it is understood by one of ordinary skill in the art that any reasonable variability is contemplated.

In an alternative embodiment, what is contemplated is the above-described nutraceutical for human consumption where the mixture further includes an organic sulfur compound. In a preferred embodiment, the organic sulfur compound is MSM.

In the preferred embodiment, a capsule includes about 10% to 25% by weight of MSM in the nutraceutical as long as the recommended dosage remains within any recommended daily dose. In another preferred embodiment, the capsule includes 17% by weight of MSM for one possible capsule formulation of 3,775 mg where the mixture includes 1,500 mg of glucosamine, 1,200 mg of chondroitin, 425 mg of tart cherry, and 650 mg of MSM for a weigh distribution in a capsule containing these four components of 40% by weight of glucosamine, 32% by weight of chondroitin sulfate, 11% by weight of tart cherries, and 17% by weight of MSM.

Other embodiments include the use of other known joint and muscle regenerative elements, or antioxidants including but not limited to melatonin, glucosamine salts, glucosamine derivatives, glucosamine hydrochloride, hyaluronic acid, chondroitin, and combinations thereof. In yet another embodiment, what is contemplated is a nutraceutical for the protection of joints and muscles, the nutraceutical being made of a mixture of two cartilage supplements and a plant-based antioxidant in a plant.

In a preferred embodiment, the two cartilage supplements are selected from the group consisting of glucosamine, glucosamine salts, glucosamine derivatives, glucosamine hydrochloride, hyaluronic acid, chondroitin, chondroitin sulfate, and combinations thereof. In another preferred embodiment, the two cartilage supplements are glucosamine and chondrointin sulfate, and the plant is selected from the group consisting of leaves, stems, roots, flowers, and fruits where a preferred fruit is tart cherry or sweet cherry.

What is also contemplated is a method of treating osteoarthritis, the method comprising the step of providing to a patient on a ongoing basis an effective level of a nutraceutical for human consumption, the nutraceutical comprising a mixture of an amino sugar, a sulfated glycosaminoglycan, and a vacuolar flavonoid pigment for regular consumption, and waiting a biologically significant period of time for pain in the joints and muscles of the patient of the nutraceutical to subside or diminish. One of ordinary skill in the art recognizes that the regular basis is fixed by a treating physicians based on scientific evidence and testimonial evidence, but in one contemplated method, a daily dose is administered to the patient. In yet another method, it is observed that daily treatment of a nutraceutical as described above relieves the pain in the joints and muscles of a patient in 30 to 60 days.

It is understood by one of ordinary skill in the art that these steps correspond to the general steps to be taken to practice this method of this disclosure. Other auxiliary steps may be taken to conduct the treatment of osteoarthritis, but they do not affect the validity and completeness of the disclosure of this general method. Persons of ordinary skill in the art appreciate that although the teachings of the disclosure have been illustrated in connection with certain embodiments and methods, there is no intent to limit the invention to such embodiments and method. On the contrary, the intention of this application is to cover all modifications and embodiments falling fairly within the scope of the teachings of the disclosure.

What is claimed is:

1. A nutraceutical comprising a powdered mixture comprising about 48% by weight of glucosamine, about 38% by weight of chondroitin sulfate, and about 14% by weight of tart cherry.

2. The nutraceutical of claim 1, wherein the tart cherry is a source of melatonin.

3. A nutraceutical mixture comprising about 40% by weight of glucosamine, about 32% by weight of chondroitin sulfate, 11% by weight of tart cherry, and about 17% by weight of methylsulfonylmethane.

\* \* \* \* \*